United States Patent [19]
Jossens et al.

[11] Patent Number: 5,603,821
[45] Date of Patent: Feb. 18, 1997

[54] LOW-ALUMINUM BORON BETA ZEOLITE

[75] Inventors: Lawrence W. Jossens, Albany; Donald S. Santilli, Larkspur; James N. Ziemer, Hercules, all of Calif.

[73] Assignee: Chevron Research Company, San Francisco, Calif.

[21] Appl. No.: 314,182

[22] Filed: Sep. 28, 1994

Related U.S. Application Data

[62] Division of Ser. No. 905,720, Jun. 26, 1992, Pat. No. 5,393,407, which is a division of Ser. No. 594,574, Oct. 9, 1990, Pat. No. 5,166,111, which is a continuation of Ser. No. 377,359, Jul. 7, 1989, abandoned.

[51] Int. Cl.$^6$ ............................ C10G 47/16; C10G 11/05
[52] U.S. Cl. ........................ 208/111; 208/108; 208/113; 208/114; 208/120
[58] Field of Search ................................ 208/108, 111, 208/113, 114, 120

[56] References Cited

U.S. PATENT DOCUMENTS

| | | | |
|---|---|---|---|
| 4,661,467 | 4/1987 | Kuehl | 502/60 |
| 4,784,749 | 11/1988 | Chang et al. | 208/120 |
| 4,788,378 | 11/1988 | Chang et al. | 208/120 |
| 5,061,466 | 10/1991 | Chang et al. | 502/61 |

Primary Examiner—Anthony McFarlane
Assistant Examiner—Walter D. Griffin
Attorney, Agent, or Firm—R. J. Sheridan

[57] ABSTRACT

A crystalline low-aluminum boron beta zeolite is prepared using a diquaternary ion as a template.

7 Claims, No Drawings

5,603,821

LOW-ALUMINUM BORON BETA ZEOLITE

This is a divisional of application Ser. No. 07/905,720, filed Jun. 26, 1992, now U.S. Pat. No. 5,193,407, which is a Divisional of application Ser. No. 07/594,574, filed Oct. 9, 1990, now U.S. Pat. No. 5,166,111, which in turn is a Continuation of application Ser. No. 377,359, filed Jul. 7, 1989, now abandoned.

BACKGROUND OF THE INVENTION

Natural and synthetic zeolitic crystalline aluminosilicates are useful as catalysts and adsorbents. These aluminosilicates have distinct crystal structures which are demonstrated by X-ray diffraction. The crystal structure defines cavities and pores which are characteristic of the different species. The adsorptive and catalytic properties of each crystalline aluminosilicate are determined in part by the dimensions of its pores and cavities. Thus, the utility of a particular zeolite in a particular application depends at least partly on its crystal structure.

Because of their unique molecular sieving characteristics, as well as their catalytic properties, crystalline aluminosilicates are especially useful in such applications as gas drying and separation and hydrocarbon conversion. Although many different crystalline aluminosilicates and silicates have been disclosed, there is a continuing need for new zeolites and silicates with desirable properties for gas separation and drying, hydrocarbon and chemical conversions, and other applications.

Crystalline aluminosilicates are usually prepared from aqueous reaction mixtures containing alkali or alkaline earth metal oxides, silica, and alumina. "Nitrogenous zeolites" have been prepared from reaction mixtures containing an organic templating agent, usually a nitrogen-containing organic cation. By varying the synthesis conditions and the composition of the reaction mixture, different zeolites can be formed using the same templating agent. Use of N,N,N-trimethyl cyclopentyl-ammonium iodide in the preparation of Zeolite SSZ-15 molecular sieve is disclosed in U.S. Pat. No. 4,610,854; use of 1-azoniaspiro [4.4] nonyl bromide and N,N,N-trimethyl neopentylammonium iodide in the preparation of a molecular sieve termed "Losod" is disclosed in Helv. Chim. Acta (1974); Vol. 57, p. 1533 (W. Sieber and W. M. Meier); use of quinuclidinium compounds to prepare a zeolite termed "NU-3" is disclosed in European Patent Publication No. 40016; use of 1,4-di(1-Azonia bicyclo [2.2.2]octane) lower alkyl compounds in the preparation of Zeolite SSZ-16 molecular sieve is disclosed in U.S. Pat. No. 4,508,837; use of N,N,N-trialkyl-1-adamantamine in the preparation of Zeolite SSZ-13 molecular sieve is disclosed in U.S. Pat. No. 4,544,538, and for SSZ-24 in U.S. Pat. No. 4,665,110.

Beta zeolite is a known synthetic crystalline aluminosilicate originally described in U.S. Pat. Nos. 3,308,069 and Re 28,341 to which reference is made for further details of this zeolite, its preparation and properties.

Synthetic zeolitic crystalline borosilicates are useful as catalysts. Methods for preparing high silica content zeolites that contain framework boron are known and disclosed in U.S. Pat. No. 4,269,813. The amount of boron contained in the zeolite usually may be made to vary by incorporating different amounts of borate ion in the zeolite forming solution.

U.S. Pat. No. 4,788,169 describes a method for preparing beta zeolite containing boron. This boron beta zeolite contains 7000 parts per million of aluminum according to the analyses given therein. European Patent Application No. 188,913 claims compositions for various intermediate pore boron-containing zeolites with an aluminum content of less than 0.05% by weight.

SUMMARY OF THE INVENTION

We have prepared a family of crystalline borosilicate molecular sieves with unique properties, referred to herein as "Low-Aluminum Boron Beta Zeolite" or simply "(B)Beta". Thus, according to the present invention, a zeolite composition, (B)Beta, is provided. Also, advantageous uses have been discovered.

(B)Beta has a mole ratio of an oxide selected from silicon oxide, germanium oxide, and mixtures thereof to an oxide selected from boron oxide or mixtures of boron oxide with aluminum, gallium, or iron oxide, greater than about 10:1 and wherein the amount of aluminum is less than 0.10% by weight and having the X-ray diffraction lines of Table 1(a) below. An aluminum-free boron beta zeolite can also be made using the novel method disclosed herein. The amount of aluminum contained in the zeolite depends simply upon the aluminum impurity present in the silica source.

This zeolite further has a composition, as synthesized and in the anhydrous state, in terms of mole ratios of oxides as follows: (1.0 to 5.0)$Q_2O$:(0.1 to 2.0)$M_2O$:$W_2O_3$:(greater than 10)$YO_2$ wherein M is an alkali metal cation, W is selected from boron, Y is selected from silicon, germanium and mixtures thereof, and Q is a diquaternary ammonium ion, or mixtures of diquarternary ammonium cation, and tetraethylammonium cation. (B)Beta zeolites preferably have a silica:boria ratio typically in the range of 10:1 to about 100:1. Higher mole ratios can be obtained by treating the zeolite with chelating agents or acids to extract boron from the zeolite lattice. The silica:boria mole ratio can also be increased by using silicon and carbon halides and other similar compounds. The boron in the crystalline network may also be replaced by aluminum, gallium or iron. Procedures for incorporating aluminum are described in U.S. Pat. Nos. 4,559,315 and 4,550,092 which are hereby incorporated by reference.

A method for preparing boron beta zeolite is described in U.S. Pat. No. 4,788,169. A tetraethyl ammonium template is used to make this zeolite which contains 7000 parts per million of aluminum. The method described in U.S. Pat. No. 4,788,169, however, cannot be used to make boron beta zeolite containing less than 1000 parts per million aluminum. Additionally, a low-aluminum boron beta zeolite cannot be made by replacing the aluminum with boron in the synthesized boron beta zeolite structure. Successful preparation of the low-aluminum boron beta zeolite requires using a new synthesis method described herein.

According to one embodiment of the present invention, a method is provided for making (B)beta zeolites, comprising preparing an aqueous mixture containing sources of a diquaternary ammonium ion, an oxide selected from boron oxide, and an oxide selected from silicon oxide, germanium oxide, and mixtures thereof, and having a composition, in terms of mole ratios of oxides, falling within the following ranges: $YO_2/W_2O_3$, 10:1 to 100:1; wherein Y is selected from silicon, germanium, and mixtures thereof, W is selected from boron, and Q is a diquaternary ammonium ion; maintaining the mixture at a temperature of at least 100° C. until the crystals of said zeolite are formed; and recovering said crystals.

Among other factors, the present invention is based on our finding that low-aluminum boron beta zeolite can be made using a diquaternary ammonium template. The structure of this zeolite is the same as the boron beta zeolite structure synthesized using the tetraethyl ammonium template in U.S. Pat. No. 4,788,169. Surprisingly, we have found that the amount of aluminum incorporated into this structure can be decreased by using a different template than the tetraethyl ammonium template used in U.S. Pat. No. 4,788,169. We have also found that this zeolite has unexpectedly outstanding hydrocarbon conversion properties, particularly including reforming properties with high sulfur tolerance.

DETAILED DESCRIPTION OF THE INVENTION (B)Beta zeolites, as synthesized, have a crystalline structure whose X-ray powder diffraction pattern shows the following characteristic lines:

TABLE 1(a)

| 2 Θ | d/n | 100 × I/I$_o$ | Shape |
|---|---|---|---|
| 7.7 | 11.5 | 25 | Broad |
| 18.40 | 4.82 | 8 | Very Broad |
| 21.44 | 4.14 | 18 | |
| 22.53 | 3.95 | 100 | |
| 27.50 | 3.24 | 10 | |
| 28.92 | 3.10 | 8 | Broad |
| 29.90 | 2.97 | 9 | |

Typical (B)Beta borosilicate and boroaluminosilicate zeolites have the X-ray diffraction pattern of Tables 2 and 4 below. The d-spacings are shown in Table 8 and demonstrate framework substitution. Calcined (B)Beta has a typical pattern as shown in Table 1(b).

TABLE 1(b)

| 2 Θ | d/n | 100 × I/I$_o$ | Shape |
|---|---|---|---|
| 7.7 | 11.5 | 85 | Broad |
| 13.58 | 6.52 | 9 | |
| 14.87 | 5.96 | 12 | Broad |
| 18.50 | 4.80 | 3 | Very Broad |
| 21.83 | 4.07 | 15 | |
| 22.87 | 3.89 | 100 | Broad |
| 27.38 | 3.26 | 10 | |
| 29.30 | 3.05 | 6 | Broad |
| 30.08 | 2.97 | 8 | |

The X-ray powder diffraction patterns were determined by standard techniques. The radiation was the K-alpha/doublet of copper and a scintillation counter spectrometer with a strip-chart pen recorder was used. The peak heights I and the positions, as a function of 2 Θ where Θ is the Bragg angle, were read from the spectrometer chart. From these measured values, the relative intensities, 100I/I$_o$, where I$_o$ is the intensity (peak height) of the strongest peak, and d/n, related to interplanar spacings in Angstroms corresponding to the recorded peaks, can be calculated. The X-ray diffraction pattern of Table 1(a) is characteristic of (B)Beta zeolites. The zeolite produced by exchanging the metal or other cations present in the zeolite with various other cations yields substantially the same diffraction pattern although there can be minor shifts in interplanar spacing and minor variations in relative intensity. Minor variations in the diffraction pattern can also result from variations in the organic compound used in the preparation and from variations in the silica-to-boria mole ratio from sample to sample. Calcination can also cause minor shifts in the X-ray diffraction pattern. Notwithstanding these minor perturbations, the basic crystal lattice structure remains unchanged.

(B)Beta zeolites can be suitably prepared from an aqueous solution containing sources of an alkali metal borate, a bis(1-Azonia, bicyclo[2.2.2] octane-α, ω alkane diquaternary ammonium ion, and an oxide of silicon or germanium, or mixture of the two. The reaction mixture should have a composition in terms of mole ratios falling within the following ranges:

| | Broad | Preferred |
|---|---|---|
| YO$_2$/W$_2$O$_3$ | 10–200 | 30–100 |
| OH/YO$_2$ | 0.10–1.0 | 0.25–0.50 |
| Q/YO$_2$ | 0.05–0.50 | 0.25–0.35 |
| M+/YO$_2$ | 0.05–0.30 | 0.05–0.10 |
| H$_2$O/YO$_2$ | 15–300 | 25–60 |
| Q/Q+M+ | 0.30–0.90 | 0.60–0.80 | wherein Q is a diquaternary ammonium ion, or mixture with tetramethylammonium cation, Y is silicon, germanium or both, and W is boron. M is an alkali metal, preferably sodium. The organic compound which acts as a source of the quaternary ammonium ion employed can provide hydroxide ion.

When using the quaternary ammonium hydroxide compound as a template, it has also been found that purer forms of (B)Beta are prepared when there is an excess of compound present relative to the amount of alkali metal hydroxide.

The bis(1-Azonia bicyclo[2.2.2]octane) a' ω alkane diquaternary ammonium ion component Q, of the crystallization mixture, is derived from the quaternary ammonium compound. Preferably, the diquaternary ammonium ion is derived from a compound of the formula:

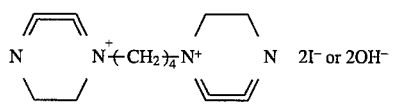

The quaternary ammonium compounds are prepared by methods known in the art, an example of which can be found in U.S. Pat. No. 4,508,837. The reaction mixture is prepared using standard zeolitic preparation techniques. Sources of boron for the reaction mixture include borosilicate glasses and most particularly, other reactive borates and borate esters. Typical sources of silicon oxide include silicates, silica hydrogel, silicic acid, colloidal silica, tetra-alkyl orthosilicates, and silica hydroxides.

The reaction mixture is maintained at an elevated temperature until the crystals of the zeolite are formed. The temperatures during the hydrothermal crystallization step are typically maintained from about 140° C. to about 200° C., preferably from about 150° C. to about 170° C. and most preferably from about 135° C. to about 165° C. The crystallization period is typically greater than one day and preferably from about three days to about seven days.

The hydrothermal crystallization is conducted under pressure and usually in an autoclave so that the reaction mixture is subject to autogenous pressure. The reaction mixture can be stirred during crystallization.

Once the zeolite crystals have formed, the solid product is separated from the reaction mixture by standard mechanical separation techniques such as filtration. The crystals are water-washed and then dried, e.g., at 90° C. to 150° C. from 8 to 24 hours, to obtain the as synthesized, (B)Beta zeolite crystals. The drying step can be performed at atmospheric or subatmospheric pressures.

During the hydrothermal crystallization step, the (B)Beta crystals can be allowed to nucleate spontaneously from the reaction mixture. The reaction mixture can also be seeded with (B)Beta crystals both to direct, and accelerate the crystallization, as well as to minimize the formation of undesired aluminosilicate contaminants.

The synthetic (B)Beta zeolites can be used as synthesized or can be thermally treated (calcined). Usually, it is desirable to remove the alkali metal cation by ion exchange and replace it with hydrogen, ammonium, or any desired metal ion. The zeolite can be leached With chelating agents, e.g., EDTA or dilute acid solutions, to increase the silica:boria mole ratio. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, Fe, and Co are particularly preferred.

The hydrogen, ammonium, and metal components can be exchanged into the zeolite. The zeolite can also be impregnated with the metals, or, the metals can be physically intimately admixed with the zeolite using standard methods known to the art. And, the metals can be occluded in the crystal lattice by having the desired metals present as ions in the reaction mixture from which the (B)Beta zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253.

Following contact with the salt solution of the desired replacing cation, the zeolite is typically washed with water and dried at temperatures ranging from 650° C. to about 315° C. After washing, the zeolite can be calcined in air or inert gas at temperatures ranging from about 200° C. to 820° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

The Beta borosilicate and subsequent metalloborosilicate can be formed into a wide variety of physical shapes. Generally speaking, the zeolite can be in the form of a powder, a granule, or a molded product, such as extrudate having particle size sufficient to pass through a 2-mesh (Tyler) screen and be retained on a 400-mesh (Tyler) screen. In cases where the catalyst is molded, such as by extrusion with an organic binder, the borosilicate can be extruded before drying, or, dried or partially dried and then extruded. The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e., combined with it, tends to improve the conversion and selectivity of the catalyst in certain organic conversion processes. Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and the kaolins commonly known as Dixie, McNamee, Georgia, and Florida clays or others in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification. In addition to the foregoing materials, the (B)Beta zeolites can be composited with porous matrix materials and mixtures of matrix materials such as silica, alumina, titania, magnesia, silica:alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia, and silica-magnesia-zirconia. The matrix can be in the form of a cogel.

The (B)Beta zeolites can also be composited with other zeolites such as synthetic and natural faujasites (e.g., X and Y), erionites, and mordenites. They can also be composited with purely synthetic zeolites such as those of the ZSM series. The combination of zeolites can also be composited in a porous inorganic matrix.

(B)Beta zeolites are useful in hydrocarbon conversion reactions. Hydrocarbon conversion reactions are chemical and catalytic processes in which carbon-containing compounds are changed to different carbon-containing compounds. Examples of hydrocarbon conversion reactions include catalytic cracking, hydrocracking, and olefin and aromatics formation reactions. The catalysts are useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., ortho xylene), and disproportionating aromatics (e.g., toluene) to provide mixtures of benzene, xylenes, and higher methylbenzenes. The (B)Beta catalysts have high selectivity, and under hydrocarbon conversion conditions can provide a high percentage of desired products relative to total products. (B)Beta zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and in general, can be any carbon containing fluid susceptible to zeolitic catalytic reactions. Depending on the type of processing, the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

Using a (B)Beta zeolite catalyst which contains boron and/or aluminum framework substitution and a hydrogenation promoter, heavy petroleum residual feedstocks, cyclic stocks, and other hydrocrackate charge stocks can be hydrocracked at hydrocracking conditions including a temperature in the range of from 175° C. to 485° C., molar ratios of hydrogen to hydrocarbon charge from 1 to 100, a pressure in the range of from 0.5 to 350 bar, and a liquid hourly space velocity (LHSV) in the range of from 0.1 to 30.

The hydrocracking catalysts contain an effective amount of at least one hydrogenation catalyst (component) of the type commonly employed in hydrocracking catalysts. The hydrogenation component is generally selected from the group of hydrogenation catalysts consisting of one or more metals of Group VIB and Group VIII, including the salts, complexes, and solutions containing such. The hydrogenation catalyst is preferably selected from the group of metals, salts, and complexes thereof of the group consisting of at least one of platinum, palladium, rhodium, iridium, and mixtures thereof or the group consisting of at least one of nickel, molybdenum, cobalt, tungsten, titanium, chromium, and mixtures thereof. Reference to the catalytically active metal or metals is intended to encompass such metal or metals in the elemental state or in some form such as an oxide, sulfide, halide, carboxylate, and the like.

The hydrogenation catalyst is present in an effective amount to provide the hydrogenation function of the hydrocracking catalyst and preferably in the range of from 0.05% to 25% by weight.

The catalyst may be employed in conjunction with traditional hydrocracking catalysts, e.g., any aluminosilicate heretofore employed as a component in hydrocracking catalysts. Representative of the zeolitic aluminosilicates disclosed heretofore as employable as component parts of hydrocracking catalysts are Zeolite Y (including steam stabilized, e.g., ultra-stable Y), Zeolite X, Zeolite beta (U.S. Pat. No. 3,308,069), Zeolite ZK-20 (U.S. Pat. No. 3,445,727), Zeolite ZSM-3 (U.S. Pat. No. 3,415,736), faujasite, LZ-10 (U.K. Patent 2,014,970, Jun. 9, 1982), ZSM-5-type zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolites, LZ-210-type zeolite, and mixtures thereof. Traditional hydrocracking catalysts containing amounts of $Na_2O$ less than about one percent by weight are generally preferred. The relative amounts of the (B)Beta component and traditional hydrocracking component, if any, will depend at least in part, on the selected hydrocarbon feedstock and on the desired product distribution to be obtained therefrom, but in all instances an effective amount of (B)Beta is employed. The hydrocracking catalysts are typically employed with an inorganic oxide matrix component which may be any of the inorganic oxide matrix components which have been employed heretofore in the formulation of hydrocracking catalysts including: amorphous catalytic inorganic oxides, e.g., catalytically active silica-aluminas, clays, silicas, aluminas, silica-aluminas, silica-zirconias, silica-magnesias, alumina-borias, alumina-titanias, and the like and mixtures thereof. The traditional hydrocracking catalyst component (TC) and (B)Beta may be mixed separately with the matrix component and then mixed or the TC component and (B)Beta may be mixed and then formed with the matrix component.

(B)Beta can be used to dewax hydrocarbonaceous feeds by selectively removing or transforming straight chain paraffins. The catalytic dewaxing conditions are dependent in large measure on the feed used and upon the desired pour point. Generally, the temperature will be between about 200° C. and about 475° C., preferably between about 250° C. and about 450° C. The pressure is typically between about 15 psig and about 3000 psig, preferably between about 200 psig and 3000 psig. The LHSV preferably will be from 0.1 to 20, preferably between about 0.2 and about 10.

Hydrogen is preferably present in the reaction zone during the catalytic dewaxing process. The hydrogen to feed ratio is typically between about 500 and about 30,000 SCF/bbl (standard cubic feet per barrel), preferably about 1,000 to about 20,000 SCF/bbl. Generally, hydrogen will be separated from the product and recycled to the reaction zone. Typical feedstocks include light gas-oil, heavy gas-oils, and reduced crudes boiling about 350° F. The (B)Beta hydrodewaxing catalyst may optionally contain a hydrogenation component of the type commonly employed in dewaxing catalysts. The hydrogenation component may be selected from the group of hydrogenation catalysts consisting of one or more metals of Group VIB and Group VIII, including the salts, complexes and solutions containing such metals. The preferred hydrogenation catalyst is at least one of the group of metals, salts, and complexes selected from the group consisting of at least one of platinum, palladium, rhodium, iridium, and mixtures thereof or at least one from the group consisting of nickel, molybdenum, cobalt, tungsten, titanium, chromium, and mixtures thereof. Reference to the catalytically active metal or metals is intended to encompass such metal or metals in the elemental state or in some form such as an oxide, sulfide, halide, carboxylate, and the like.

The hydrogenation component is present in an effective amount to provide an effective hydrodewaxing catalyst preferably in the range of from about 0.05 to 5% by weight.

(B)Beta can be used to convert straight run naphthas and similar mixtures to highly aromatic mixtures. Thus, normal and slightly branched chained hydrocarbons, preferably having a boiling range above about 40° C. and less than about 200° C., can be converted to products having a substantial aromatics content by contacting the hydrocarbon feed with the zeolite at a temperature in the range of from about 400° C. to 600° C., preferably 480° C.–550° C. at pressures ranging from atmospheric to 10 bar, and LHSV ranging from 0.1 to 15. The hydrogen to hydrocarbon ratio will range between 1 and 10. (B)Beta can be used in a fixed, fluid or moving bed reformer. The conversion catalyst preferably contain a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. The most preferred metal is platinum. The amount of Group VIII metal present in the conversion catalyst should be within the normal range of use in reforming catalysts, from about 0.05 to 2.0 wt. %, preferably 0.2 to 0.8 wt. %. The performance of the noble metal in (B)Beta may be further enhanced by the presence of other metals as promotors for aromatization selectivity.

The zeolite/Group VIII metal conversion catalyst can be used without a binder or matrix. The preferred inorganic matrix, where one is used, is a silica-based binder such as Cab-O-Sil or Ludox. Other matrices such as magnesia and titania can be used. The preferred inorganic matrix is nonacidic.

It is critical to the selective production of aromatics in useful quantities that the conversion catalyst be substantially free of acidity, for example, by poisoning the zeolite with a basic metal, e.g., alkali metal, compound. The zeolite is usually prepared from mixtures containing alkali metal hydroxides and thus, have alkali metal contents of about 1–2 wt. %. These high levels of alkali metal, usually sodium or potassium, are unacceptable for most catalytic applications because they greatly deactivate the catalyst for cracking reactions. Usually, the alkali metal is removed to low levels by ion exchange with hydrogen or ammonium ions. By alkali metal compound as used herein is meant elemental or ionic alkali metals or their basic compounds. Surprisingly, unless the zeolite itself is substantially free of acidity, the basic compound is required in the present process to direct the synthetic reactions to aromatics production. In the case of (B)Beta the intrinsic cracking acidity is quite low and neutralization is not usually required.

We have also found that (B)Beta is advantageously used to catalytically crack hydrocarbon feedstocks in the absence of hydrogen. Preferred conditions involve a fluidized catalytic cracking process which consists of contacting a hydrocarbon feedstock with a catalyst in a reaction zone in the absence of added hydrogen at average catalyst temperatures ranging from 800° F. to 1500° F., separating the catalyst from the product effluent, introducing the catalyst into a steam-stripping zone, and subsequently into a regeneration zone in the presence of steam and free oxygen containing gas where reaction coke deposited on the catalyst is burned off at elevated temperatures ranging from 1000° F. to 1550° F., and then recycling the reactivated catalyst to the reaction zone.

For this purpose, the (B)Beta can be employed in conjunction with traditional cracking catalysts either as an incorporated constituent component or as a separate additive particle.

The catalyst may be employed in conjunction with traditional cracking catalysts, comprising any aluminosilicate heretofore employed as a component in cracking catalysts, preferably having a pore size greater than 8.0 angstroms. Representative of the zeolitic aluminosilicates disclosed heretofore as employable as component parts of cracking catalysts are Zeolite Y (including steam stabilized Y, rare earth Y, chemically modified Y, ultra-stable Y or combinations thereof), zeolite X, Zeolite beta (U.S. Pat. No. 3,308,069), Zeolite ZK-20 (U.S. Pat. No. 3,445,727), Zeolite ZSM-3 (U.S. Pat. No. 3,415,736), faujasite, LZ-10 (U.K. Patent 2,014,970, Jun. 9, 1982), ZSM-5-Type Zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolite, LZY-210 type zeolite or other dealuminated zeolite of 24.5 Å unit cell size or lower, or zeolite grown "in-situ" in matrix materials (U.S. Pat. Nos. 3,647,718 and 4,493,902), and the mixtures thereof. The term "zeolite" as used herein contemplates not only aluminosilicates but substances in which the aluminum is replaced by gallium or boron and substances in which silicon is replaced by germanium. Other representative acidic aluminosilicates also deemmed employable as component parts are amorphous silica-alumina catalysts, synthetic mica-montmorillonite catalysts (as defined in U.S. Pat. No. 3,252,889), cross-linked or pillared clays (as defined in U.S. Pat. Nos. 4,176,090; 4,248,739; 4,238,364 and 4,216,188), and acid activated clays—bentonite, hectorite, saponite.

Traditional cracking catalysts containing amounts of $Na_2O$ less than about one percent by weight are generally preferred. The relative amounts of the (B)Beta component and traditional cracking component (TC), if any, will depend at least in part, on the selected hydrocarbon feedstock and on the desired product distribution to be obtained therefrom, but in all instances, an effective amount of (B)Beta is employed. When a TC component is employed, the relative weight ratio of the TC to the (B)Beta is generally between about 1:10 and about 500:1, desirably between about 1:10 and about 200:1, preferably between about 1:2 and about 50:1, and most preferably is between about 1:1 and about 20:1.

The cracking catalysts are typically employed with an inorganic oxide matrix component which may be any of the inorganic oxide matrix components which have been employed heretofore in the formulation of FCC catalysts including: amorphous catalytic inorganic oxides, e.g., catalytically active silica-aluminas, clays, synthetic or acid activated clays, silicas, aluminas, silica-aluminas, silica-zirconias, silica-magnesias, alumina-borias, alumina-titanias, pillared or cross-linked clays, and the like and mixtures thereof. The TC component and (B)Beta may be mixed separately with their respective matrix component and then mixed together or the TC component and (B)Beta may be mixed together and then formed with the matrix component.

The mixture of a traditional cracking catalyst and (B)Beta may be carried out in any manner which results in the coincident presence of such in contact with the crude oil feedstock under catalytic cracking conditions. For example, a catalyst may be employed containing the traditional cracking catalyst component and (B)Beta in single catalyst particles or (B)Beta with or without a matrix component may be added as a discrete component to a traditional cracking catalyst provided its particle has appropriate density and particle size distribution.

(B)Beta can also be used to oligomerize straight and branched chain olefins having from about 2–21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous state phase with (B)Beta at a temperature of from about 450° F. to about 1200° F., a WHSV of from about 0.2 to about 50 and a hydrocarbon partial pressure of from about 0.1 to about 50 atmospheres.

Also, temperatures below about 450° F. may be used to oligomerize the feedstock, when the feedstock is in the liquid phase when contacting the zeolite catalyst. Thus, when the olefin feedstock contacts the zeolite catalyst in the liquid phase, temperatures of from about 50° F. to about 450° F., and preferably from 80°–400° F. may be used and a WHSV of from about 0.05 to 20 and preferably 0.1 to 10. It will be appreciated that the pressures employed must be sufficient to maintain the system in the liquid phase. As is known in the art, the pressure will be a function of the number of carbon atoms of the feed olefin and the temperature. Suitable pressures include from about 0 psig to about 3000 psig.

The zeolite can have the original cations associated therewith replaced by a wide variety of other cations according to techniques well known in the art. Typical cations would include hydrogen, ammonium, and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20 wt. %. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 which is incorporated totally herein by reference. If required, such zeolites may be obtained by steaming, by use in a conversion process or by any other method which may occur to one skilled in this art.

(B)Beta can be used to convert light gas $C_2$–$C_6$ paraffins and/or olefins to higher molecular weight hydrocarbons including aromatic compounds. Operating temperatures of 100°–700° C., operating pressures of 0–1000 psig and space velocities of 0.5-40 $hr^{-1}$ WHSV can be used to convert the $C_2$–$C_6$ paraffin and/or olefins to aromatic compounds. Preferably, the zeolite will contain a catalyst metal or metal oxide wherein said metal is selected from the group consisting of Group IB, IIB, VIII, and IIIA of the Periodic Table, and most preferably, gallium or zinc and in the range of from about 0.05–5 wt. %.

(B)Beta can be used to condense lower aliphatic alcohols having 1–10 carbon atoms to a gasoline boiling point hydrocarbon product comprising mixed aliphatic and aromatic hydrocarbon. The condensation reaction proceeds at a temperature of about 500°–1000° F., a pressure of about 0.5–1000 psig and a space velocity of about 0.5–50 WHSV. The process disclosed in U.S. Pat. No. 3,984,107 more specifically describes the process conditions used in this process, which patent is incorporated totally herein by reference.

The catalyst may be in the hydrogen form or may be base exchanged or impregnated to contain amonium or a metal cation complement, preferably in the range of from about 0.05–5 wt. %. The metal cations that may be present include any of the metals of the Groups I–VIII of the Periodic Table. However, in the case of Group IA metals, the cation content should in no case be so large as to effectively inactivate the catalyst.

The catalyst can be made highly active and highly selective for isomerizing $C_4$ to $C_7$ hydrocarbons. The activity means that the catalyst can operate at relatively low temperatures which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst with a hydrocarbon feed under isomerization conditions. The feed is preferably a light straight run fraction, boiling within the range of 30°–250° F. and preferably from 60°–200° F. Preferably, the hydrocarbon feed for the process comprises a substantial amount of $C_4$ to $C_7$ normal and slightly branched low octane hydrocarbons, more preferably $C_5$ and $C_6$ hydrocarbons.

The pressure in the process is preferably between 50–1000 psig, more preferably between 100–500 psig. The LHSV is preferably between about 1 to about 10 with a value in the range of about 1 to about 4 being more preferred. It is also preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. The temperature is preferably between about 200° F. and about 1000° F., more preferably between 400°–600° F. As is well known to those skilled in the isomerization art, the initial selection of the temperature within this broad range is made primarily as a function of the desired conversion level considering the characteristics of the feed and of the catalyst. Thereafter, to provide a relatively constant value for conversion, the temperature may have to be slowly increased during the run to compensate for any deactivation that occurs.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. An example of a suitable catalyst for this hydrodesulfurization process is an alumina-containing support and a minor catalytic proportion of molybdenum oxide, cobalt oxide and/or nickel oxide. A platinum on alumina hydrogenating catalyst can also work. In which case, a sulfur sorber is preferably placed downstream of the hydrogenating catalyst, but upstream of the present isomerization catalyst. Examples of sulfur sorbers are alkali or alkaline earth metals on porous refractory inorganic oxides, zinc, etc. Hydrodesulfurization is typically conducted at 315°–455° C., at 200–2000 psig, and at a LHSV of 1–5.

It is preferable to limit the nitrogen level and the water content of the feed. Catalysts and processes which are suitable for these purposes are known to those skilled in the art.

After a period of operation, the catalyst can become deactivated by coke. Coke can be removed by contacting the catalyst with an oxygen-containing gas at an elevated temperature.

The isomerization catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is the amount of Group VIII metal present in the conversion catalyst should be within the normal range of use in isomerizing catalysts, from about 0.05–2.0 wt. %.

(B)Beta can be converted to a catalyst for use in a process for the alkylation or transalkylation of an aromatic hydrocarbon. The process comprises contacting the aromatic hydrocarbon with a $C_2$ to $C_{20}$ olefin alkylating agent or a polyalkyl aromatic hydrocarbon transalkylating agent, under at least partial liquid phase conditions, and in the presence of a catalyst comprising (B)Beta. For high catalytic activity, the (B)Beta zeolite should be predominantly in its hydrogen ion form. Generally, the zeolite is converted to its hydrogen form by ammonium exchange followed by calcination. If the zeolite is synthesized with a high enough ratio of organo-nitrogen cation to sodium ion, calcination alone may be sufficient. It is preferred that, after calcination, at least 80% of the cation sites are occupied by hydrogen ions and/or rare earth ions.

The pure (B)Beta zeolite may be used as a catalyst, but generally, it is preferred to mix the zeolite powder with an inorganic oxide binder such as alumina, silica, silica/alumina, or naturally occurring clays and form the mixture into tablets or extrudates. The final catalyst may contain from 1–99 wt. % (B)Beta zeolite. Usually the zeolite content will range form 10–90 wt. %, and more typically from 60–80 wt. %. The preferred inorganic binder is alumina. The mixture may be formed into tablets or extrudates having the desired shape by methods well known in the art.

Examples of suitable aromatic hydrocarbon feedstocks which may be alkylated or transalkylated by the process of the invention include aromatic compounds such as benzene, toluene, and xylene. The preferred aromatic hydrocarbon is benzene. Mixtures of aromatic hydrocarbons may also be employed.

Suitable olefins for the alkylation of the aromatic hydrocarbon are those containing 2–20 carbon atoms, such as ethylene, propylene, butene-1, transbutene-2, and cis-butene-2, and higher olefins or mixtures thereof. The preferred olefin is propylene. These olefins may be present in admixture with the corresponding $C_2$ to $C_{20}$ paraffins, but it is preferable to remove any dienes, acetylenes, sulfur compounds or nitrogen compounds which may be present in the olefin feedstock stream to prevent rapid catalyst deactivation.

When transalkylation is desired, the transalkylating agent is a polyalkyl aromatic hydrocarbon containing two or more alkyl groups that each may have from two to about four carbon atoms. For example, suitable polyalkyl aromatic hydrocarbons include di-, tri-, and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

Reaction products which may be obtained include ethylbenzene from the reaction of benzene with either ethylene or polyethylbenzenes, cumene from the reaction of benzene with propylene or polyisopropylbenzenes, ethyltoluene from the reaction of toluene with ethylene or polyethyltoluenes, cymenes from the reaction of toluene with propylene or polyisopropyltoluenes, and secbutylbenzene from the reaction of benzene and n-butenes or polybutylbenzenes. The production of cumene from the alkylation of benzene with propylene or the transalkylation of benzene with di-isopropylbenzene is especially preferred.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100°–600° F., preferably, 250°–450° F. The reaction pressure should be sufficient to maintain at least a partial liquid phase in order to retard catalyst fouling. This is typically 50–1000 psig depending on the feedstock and reaction temperature. Contact time may range from 10 seconds to 10 hours, but is usually from five minutes to an hour. The WHSV in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100°–600° F., but it is preferably about 250°–450° F. The reaction pressure should be sufficient to maintain at least a partial liquid phase, typically in the range of about 50–1000 psig, preferably 300–600 psig. The WHSV will range from about 0.1–10.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., platinum, include hydrogenation-dehydrogenation reactions, denitrogenation, and desulfurization reactions. Some hydrocarbon conversions can be carried out on (B)Beta zeolites utilizing the large pore shape-selective behavior. For example, the substituted-(B)Beta zeolite may be used in preparing cumene or other alkylbenzenes in processes utilizing propylene to alkylate aromatics.

(B)Beta can be used in hydrocarbon conversion reactions with active or inactive supports, with organic or inorganic binders, and with and without added metals. These reactions are well known to the art, as are the reaction conditions.

(B)Beta can also be used as an adsorbent, as a filler in paper, paint, and toothpastes, and as a water-softening agent in detergents.

The following examples illustrate the preparation and use of (B)Beta.

EXAMPLES

Example 1

Synthesis of an Effective Diquaternary Ammonium Compound Boron Beta Crystallization 48 grams of DABCO (1,4 Diazabicyclo [2.2.2] octane) is stirred into 800 ml of Ethyl Acetate. 42 grams of 1,4 Diiodobutane is added dropwise and slowly while the reaction is stirred. Allowing the reaction to run for a few days at room temperature produces a high yield of the precipitated diquaternary compound,

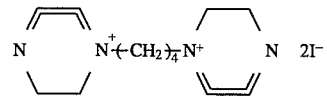

The product is washed with THF and then ether and then vacuum dried. Melting point=255° C.

The crystalline salt is conveniently converted to the hydroxide form by stirring overnight in water with AGI-X8 hydroxide ion exchange resin to achieve a solution ranging from 0.25–1.5 molar.

Example 2

10.85 g of a 0.90M solution of the template from Example 1 is diluted with 3.95 ml $H_2O$. 0.23 g of $Na_2B_4O_7.18H_2O$ are dissolved in this solution and then 1.97 g of Cabosil M5 are blended in last. The reaction mixture is heated in a Parr 4745 reactor at 150° C. and rotated at 43 rpm on a spit in a Blue M oven over a 9-day period. The solid component of the reaction is filtered, washed repeatedly, dried at 115° C. and analyzed by X-ray diffraction. The product is identified as (B)Beta.

Example 3

The same experiment is set up as in Example 2 except the diquat in Example 2 is replaced by an equivalent amount of TEAOH. The experiment is run under analogous conditions although this time the crystallization is complete in 6 days. The product is ZSM-5 by XRD. This shows that TEAOH doesn't have enough selectivity for Beta in the borosilicate system. TEAOH is the template used in the prior art for synthesis of Beta.

Example 4

202 g of a 0.84M solution of the template from Example 1 is mixed with 55 g of $H_2O$, and 4.03 g of $Na_2B_4O_7 \cdot 10H_2O$. 35 g of Cabosil M5 is blended in last and the reaction is run in a Parr 600-cc stirred autoclave with liner for 6 days at 150° C. and stirred at 50 rpm. The product is well-crystallized Boron Beta. The pattern is tabulated in Table 2.

TABLE 2

| 2 Θ | d/n | Int. |
|---|---|---|
| 7.7 | 11.5 | 28 B |
| 18.40 | 4.82 | 8 VB |
| 21.44 | 4.14 | 22 |
| 22.53 | 3.95 | 120 |
| 25.50 | 3.49 | 7 |
| 26.08 | 3.42 | 3 B |
| 27.50 | 3.24 | 11 |
| 28.92 | 3.10 | 9 B |
| 29.90 | 2.97 | 10 |
| 30.57 | 2.93 | 3 |
| 31.15 | 2.86 | 2 VB |
| 33.62 | 2.67 | 6 |
| 35.17 | 2.55 | 2 |
| 36.32 | 2.47 | 2 |

B = Broad
VB = Very Broad

Examples 5–10 are given in Table 3, demonstrating the utility of the method of the invention. Examples 5–7 show that (B)Beta can be made at very low $SiO_2/B_2O_3$ values and that higher values eventually lead to some ZSM-12 formation as well. Example 8 shows that the desired product can be obtained using Ludox AS-30 as silica source. Now the aluminum impurity has risen to 530 ppm. Examples 9 and 10 show that providing the diquat as a salt to supplement TEAOH can insure formation of pure Boron Beta. Example 9 shows that is the case even without seeding.

Table 4 shows the XRD data for the product of Example 5 and Table 5 is of Example 6, both in the as-synthesized form.

TABLE 4

| 2 Θ | d/n | Int. |
|---|---|---|
| 7.7 | 11.5 | 28 B |
| 18.55 | 4.78 | 8 VB |
| 21.55 | 4.12 | 22 |
| 22.60 | 3.93 | 110 |
| 25.60 | 3.48 | 4 |
| 26.00 | 3.43 | 3 B |
| 27.58 | 3.24 | 8 |
| 29.00 | 3.08 | 6 B |
| 29.98 | 2.98 | 6 |
| 30.65 | 2.92 | 2 |
| 31.15 | 2.87 | 1 VB |
| 33.67 | 2.66 | 4 B |
| 35.27 | 2.55 | 2 |
| 36.50 | 2.47 | 2 B |

B = Broad
VB = Very Broad

TABLE 5

| 2 Θ | d/n | Int. |
|---|---|---|
| 7.7 | 11.5 | 27 B |
| 18.45 | 4.82 | 5 VB |
| 21.47 | 4.14 | 18 |
| 22.56 | 3.94 | 128 |
| 25.53 | 3.49 | 6 |
| 26.00 | 3.43 | 3 B |
| 27.52 | 3.24 | 9 |
| 28.97 | 3.09 | 7 B |
| 29.92 | 2.99 | 8 |
| 30.60 | 2.92 | 2 |
| 31.20 | 2.83 | 2 VB |
| 33.66 | 2.66 | 5 |
| 35.17 | 2.55 | 2 |
| 36.35 | 2.47 | 2 B |

B = Broad
VB = Very Broad

XRD patterns for the calcined products of Examples 5 and 6 appear in Tables 6 and 7, respectively.

The presence of the boron in the framework of beta zeolite can be indicated by changes in d-spacings. Table 8 compares the d-spacings before and after calcination for some of the

TABLE 3

| Example No. | Template (Exam. 1) | TEAOH | $H_2O$ | $Na_2B_4O_7 \cdot 10H_2O$ | $S:O_2$ | Seeded | $SiO_2/B_2O_3$ | Product |
|---|---|---|---|---|---|---|---|---|
| 5[a] | 5.60 g (0.70 m) | — | 0.30 g | 0.16 | Cabosil = 0.79 g | Yes | 15 | Beta |
| 6[a] | 5.60 g | — | 0.30 g | 0.10 | Cabosil = 0.79 g | Yes | 25 | Beta |
| 7[a] | 5.60 g | — | 0.30 g | 0.035 | Cabosil = 0.79 g | Yes | 75 | Beta + ZSM-12 |
| 8[b] | 107 g (0.467 m) | — | — | 1.15 g | Ludox AS-30 = 33.3 g | Yes | 30 | Beta |
| 9[a] | 1.6 g Salt[c] | 40% = 3.16 g | 9.38 g | 0.20 | Cabosil = 1.75 g | No | 30 | Beta |
| 10[b] | 28.5 g[c] | 40% = 364 g | 616 g | 22.6 g | Ludox AS-30 = 660 g | No | 30 | Beta |

[a]150° C., 11 days, 0 rpm.
[b]150° C., 6 days, 50 rpm.
[c]Diquat provided as salt first prepared in Example 1 and not OH⁻ exchanged.

sharper peaks of the products of Examples 4, 5 and 6. Also shown are the values for an aluminum beta zeolite prepared by the prior art reference (Re 28,341). It can be seen that the Boron Betas show d-spacings consistently smaller than the aluminum Beta.

TABLE 6

| 2 Θ | d/n | Int. | |
|---|---|---|---|
| 7.7 | 11.5 | 34 | B |
| 13.58 | 6.53 | 3 | |
| 14.88 | 5.97 | 5 | B |
| 18.60 | 4.77 | 2 | VB |
| 21.85 | 4.06 | 10 | B |
| 22.89 | 3.88 | 42 | |
| 25.80 | 3.45 | 5 | B |
| 27.38 | 3.26 | 5 | |
| 29.35 | 3.05 | 2 | B |
| 30.10 | 2.97 | 3 | |
| 31.15 | 2.87 | 1 | VB |
| 34.00 | 2.64 | 1 | VB |
| 36.90 | 2.44 | 1 | VB |

B = Broad
VB = Very Broad

TABLE 7

| 2 Θ | d/n | Int. | |
|---|---|---|---|
| 7.7 | 11.5 | 38 | B |
| 13.52 | 6.55 | 4 | |
| 14.85 | 5.95 | 5 | B |
| 18.50 | 4.82 | 2 | VB |
| 21.80 | 4.08 | 5 | B |
| 22.82 | 3.90 | 50 | |
| 25.75 | 3.46 | 6 | B |
| 27.35 | 3.26 | 5 | |
| 29.27 | 3.05 | 2 | B |
| 30.00 | 2.98 | 4 | |
| 31.00 | 2.88 | 2 | VB |
| 33.90 | 2.64 | 2 | VB |
| 36.80 | 2.44 | 1 | VB |

B = Broad
VB = Very Broad

TABLE 8

| | Uncalcined | | | Calcined | | |
|---|---|---|---|---|---|---|
| | d/n | d/n | d/n | d/n | d/n | d/n |
| Al-B | 3.97 | 3.30 | 3.03 | 3.97 | 3.30 | 3.03 |
| Ex 4 0.07 B-B | 3.95 | 3.24 | 2.99 | 3.89 | 3.26 | 2.97 |
| Ex 6 0.10 B-B | 3.94 | 3.24 | 2.99 | 3.90 | 3.26 | 2.98 |
| Ex 5 0.13 B-B | 3.93 | 3.24 | 2.98 | 3.88 | 3.26 | 2.97 |

Note: d/n spacings for B-Betas are consistently less than those for Al-Betas.

Example 11

The product of Example 4 was calcined as follows. The sample was heated in a muffle furnace in nitrogen from room temperature up to 540° C. at a steadily increasing rate over a 7-hour period. The sample was maintained at 540° C. for four more hours and then taken up to 600° C. for an additional four hours. Nitrogen was passed over the zeolite at a rate of 20 standard cfm during heating. The calcined product had the X-ray diffraction lines indicated in Table 9 below.

TABLE 9

| 2 Θ | d/n | Int. | |
|---|---|---|---|
| 7.7 | 11.5 | 58 | B |
| 13.58 | 6.52 | 6 | |
| 14.87 | 5.96 | 8 | B |
| 18.50 | 4.80 | 2 | VB |
| 21.83 | 4.07 | 10 | B |

TABLE 9-continued

| 2 Θ | d/n | Int. | |
|---|---|---|---|
| 22.87 | 3.89 | 70 | |
| 25.75 | 3.46 | 7 | |
| 27.38 | 3.26 | 7 | |
| 29.30 | 3.05 | 4 | B |
| 30.08 | 2.97 | 5 | |
| 31.00 | 2.88 | 3 | B |
| 33.95 | 2.64 | 2 | VB |

B = Broad
VB = Very Broad

Example 12

Ion exchange of the calcined material from Example 4 was carried out using $NH_4NO_3$ to convert the zeolites from Na form to $NH_4$. Typically the same mass of $NH_4NO_3$ as zeolite was slurried into $H_2O$ at ratio of 50:1 $H_2O$ zeolite. The exchange solution was heated at 100° C. for two hours and then filtered. This process was repeated two times. Finally, after the last exchange, the zeolite was washed several times with $H_2O$ and dried.

Example 13

Constraint Index Determination 0.50 g of the hydrogen form of the zeolite of Example 4 (after treatment according to Examples 11 and 12 was packed into a ⅜-inch stainless steel tube with alundum on both sides of the zeolite bed. A Lindburg furnace was used to heat the reactor tube. Helium was introduced into the reactor tube at 10 cc/minute and atmospheric pressure. The reactor was taken to 250° F. for 40 minutes and then raised to 800° F. Once temperature equilibration was achieved a 50/50, w/w feed of n-hexane and 3-methylpentane was introduced into the reactor at a rate of 0.62 cc/hour. Feed delivery was made via syringe pump. Direct sampling onto a gas chromatograph was begun after 10 minutes of feed introduction. Constraint Index values were calculated from gas chromatographic data using methods known in the art.

| Example No. | C.I. | Conversion at 10 Min. | Temp., °F. |
|---|---|---|---|
| 13 | — | 0 | 800 |

Example 14

The product of Example 4 after treatment as in Examples 11 and 12 is refluxed overnight with $Al(NO_3)_3.9H_2O$ with the latter being the same mass as the zeolite and using the same dilution as in the ion exchange of Example 12. The product is filtered, washed, and calcined to 540° C. After pelletizing the zeolite powder and retaining the 20–40 mesh fraction, the catalyst is tested as in Example 13. Data for the reaction is given in Table 10 along with a variety of catalysts made from analogous treatments with other metal salts.

Examples 15–22

Please refer to Table 10 and Table 11.

TABLE 10

Constraint Index Determination For Metal-Treated (B)Beta

| Example No. | Metal Salt | C.I. | Conversion, % (10 Min.) | Temp., °F. |
|---|---|---|---|---|
| 13 | None | — | 0 | 800 |
| 14 | AL(NO$_3$)$_3$ | 1.0 | 35.0 | 600 |
| 15 | Ga(NO$_3$)$_3$ | 0.25 | 83.0 | 800 |
| 16 | Sn(AC)$_2$ | 0.70 | 1.0 | 800 |
| 17 | MgCL$_2$.6H$_2$O | 2.0 | 0.2 | 800 |
| 18 | Co(NO$_3$)$_2$.6H$_2$O | 1.0 | 5.0 | 800 |

Table 11 shows the data for the treatment of the product of Examples 4, 11, 12 with various quantities of Zn(Ac)$_2$.2H$_2$O.

TABLE 11

| Example No. | (B)Beta | Zn(AC)$_2$.2H$_2$O | Wt. % Zn after exch./calc. |
|---|---|---|---|
| 19 | 4.5 g | 2.20 g | 3.12 |
| 20 | 4.5 g | 1.10 g | 1.95 |
| 21 | 4.5 g | 0.55 g | 1.38 |
| 22 | 4.5 g | 0.25 9 | 0.76 |

Example 20 gave 5% conversion at 800° F. for C.I. test and CI=0.30.

Example 23

The borosilicate version of (B)Beta was evaluated as a reforming catalyst. The zeolite powder was impregnated with Pt(NH$_3$)$_4$.2NO$_3$ to give 0.8 wt. % Pt. The material was calcined up to 550° F. in air and maintained at this temperature for three hours. The powder was pelletized on a Carver press at 1000 psi and broken and meshed to 24–40.

The catalyst was evaluated at 900° F. in hydrogen under the following conditions:

```
psig = 200
H₂/HC = 6.4
WHSV = 6
Temperature = 900° F.
```

The feed was an iC$_7$ mixture (Philips Petroleum Company).

Table 12 gives data at 800° and 900° F. and 50 and 200 psig.

TABLE 12$^{(a)}$

| Temperature | 800° F. | 800° F. | 900° F. |
|---|---|---|---|
| Pressure(H$_2$) | 200 | 50 | 200 |
| Conversion % | 88.8 | 77.0 | 100 |
| Aromatization Selectivity % | 25.4 | 54.5 | 25.3 |
| Product Toluene wt. % | 19.1 | 39.3 | 16.9 |
| % Toluene in C$_5$ Aromatics | 84.9 | 93.7 | 67.8 |
| C$_5$+ yield wt. % | 46.9 | 77.4 | 30.2 |
| C$_5$-C$_8$ RON | 89.5 | 90.6 | 104.3 |

$^{(a)}$The Catalyst is quite stable and the values are averaged over at least 20 hours of run time.

Example 24

The product of Example 18 now contained a second metal due to cobalt incorporation. The catalyst was calcined to 1000° F. Next, a reforming catalyst was prepared as in Example 23. The catalyst was evaluated under the following conditions:

```
psig = 100, 200
H₂/HC = 6.4
WHSV = 12
Temperature = 800° F.
```

The feed has an iC$_7$ mixture (Philips Petroleum Company). The data for the run is given in Table 13. After 23 hours onstream, the pressure was dropped to 100 psig and this data also appears in the table. By comparison with Example 23, the incorporation of cobalt into the zeolite gives a more C$_5$+ selective reforming catalyst. The catalyst has good stability at 800° F.

TABLE 13

| Temperature | 800° F. | 800° F. |
|---|---|---|
| Pressure H$_2$ | 200 | 100 |
| Conversion % | 83.3 | 86 |
| Aromatization Selectivity % | 27 | 37 |
| Product Toluene, wt. % | 18.8 | 27.3 |
| % Toluene in C$_5$+ Aromatics | 83.3 | 85.9 |
| C$_5$+ yield, % | 59.8 | 63.7 |
| C$_5$-C$_8$ RON | 85.3 | 90.3 |

Example 25

A product was prepared as in Example 12. Next, the catalyst was dried at 600° F., cooled in a closed system, and then vacuum impregnated with an aqueous solution of Pd(NH$_3$)$_4$.2NO$_3$ to give 0.5 wt. % loading of palladium. The catalyst was then calcined slowly, up to 900° F. in air and held there for three hours. Table 14 gives run conditions and product data for the hydrocracking of hexadecane. The catalyst is quite stable at the temperatures given.

TABLE 14

| Temperature, °F. | 625 | 637 |
|---|---|---|
| WHSV | 1.55 | 1.55 |
| psig | 1200 | 1200 |
| Conversion | 85.1 | 97.8 |
| Isom. Select. | 94.5 | 69.9 |
| Crack. Select. | 5.6 | 30.1 |
| C$_5$+/C$_4$ | 10.8 | 11.5 |
| C$_5$+C$_6$/C$_5$+ | 17.8 | 17.1 |

The data shows that the catalyst has good isomerization selectivity and that the liquid yield is high compared with the gas make.

Example 26

The hydrogen form of (B)Beta can be used in typical fluidized catalytic cracking (FCC). (B)Beta, as prepared in Examples 2, 11, 12 and refluxed with Al(NO$_3$)$_3$.9H$_2$O as in Example 14, was formulated into a spray dried FCC catalytic octane additive and tested in a fixed fluidized cyclic reactor. For this example, the FCC catalytic octane additive contained nominally 25% by weight (B)Beta, 32.5% Kaolin and 42.5% silica/alumina matrix. Fixed fluidized cyclic testing was conducted at 7 cat/oil ratio, with a 1100° F. initial catalyst temperature. A subsequent gas chromatographic analysis of the liquid product was made to determine calculated octanes. The catalyst inventory during the fixed fluidized cyclic testing of the (B)Beta FCC catalytic octane additive contained 90% steamed rare earth FCC catalyst and 10% of calcined (B)Beta FCC catalytic octane additive.

Feed properties of the gas oil used during fixed fluidized cyclic testing are given in Table 15.

TABLE 15

| API Gravity | 27.43 |
|---|---|
| Aniline Point | 187.3 |
| Total Nitrogen | 1040 ppm |
| Simulated Distillation | |
| ST | 160° C. |
| 5 Vol % | 256° C. |
| 10% | 287° C. |
| 30% | 362° C. |
| 50% | 430° C. |
| 70% | 499° C. |
| 90% | 595° C. |
| 95% | 630° C. |
| EP | 654° C. |

Table 16 shows calculated research and motor octane numbers from the fixed fluidized cyclic tests.

TABLE 16

| | Reference Catalyst | 25% (B)Beta Plus Reference Catalyst |
|---|---|---|
| $C_5$-250 | | |
| RON | 85.6 | 87.8 |
| MON | 75.9 | 76.8 |
| $C_5$-340 | | |
| RON | 85.3 | 87.5 |
| MON | 75.6 | 76.9 |

What is claimed is:

1. A hydrocracking process comprising contacting a hydrocarbonaceous feedstock under hydrocracking conditions with hydrogen and a hydrocracking catalyst composition comprising a zeolite having a mole ratio of an oxide selected from silicon oxide, germanium oxide, and mixtures thereof to an oxide selected from boron oxide, or mixtures of boron oxide with aluminum oxide, gallium oxide or iron oxide, greater than 10:1 and wherein the amount of aluminum is less than 0.10% by weight and having the x-ray diffraction lines of Table 1(b), and an effective amount of a hydrogenation catalyst comprising a Group VIB metal, Group VIII metal or mixtures thereof.

2. A catalytic cracking process comprising the step of contacting a hydrocarbon feedstock in a reaction zone under catalytic cracking conditions in the absence of added hydrogen with a catalyst comprising a zeolite having a mole ratio of an oxide selected from silicon oxide, germanium oxide, and mixtures thereof to an oxide selected from boron oxide, or mixtures of boron oxide with aluminum oxide, gallium oxide or iron oxide, greater than 10:1 and wherein the amount of aluminum is less than 0.10% by weight and having the x-ray diffraction lines of Table 1(b).

3. A process in accordance with claim 2 wherein said catalyst comprises, in addition to said zeolite an aluminosilicate cracking catalyst.

4. A process as defined in claim 3 wherein the aluminosilicate cracking catalyst has a pore size greater than 8.0 angstroms.

5. A process in accordance with claim 3 wherein the catalyst composition comprises a physical mixture.

6. A process in accordance with claim 3 wherein said zeolite is incorporated in an inorganic oxide selected from the group consisting of silica, alumina, amorphous silica-alumina, silica-magnesia, silica-zirconia, alumina-boria, alumina-titanate, a synthetic clay, natural clays, acid activated clays, pillared or cross-linked clays, and mixtures thereof.

7. A process in accordance with claim 3 wherein the zeolite and cracking catalyst are incorporated in an inorganic matrix comprised of an inorganic oxide selected from the group consisting of silica, alumina, amorphous silica-alumina, silica-magnesia, silica-zirconia, alumina-boria, alumina-titanate, a synthetic clay, natural clays, acid activated clays, pillared or cross-linked clays, and mixtures thereof.

* * * * *